United States Patent [19]

Pettijohn et al.

[11] Patent Number: 5,196,622
[45] Date of Patent: Mar. 23, 1993

[54] ALKENE ADDITION PROCESS

[75] Inventors: Ted M. Pettijohn; Mark E. Lashier, both of Bartlesville, Okla.

[73] Assignee: Phillips Petroleum Company, Bartlesville, Okla.

[21] Appl. No.: 796,142

[22] Filed: Nov. 22, 1991

[51] Int. Cl.$^5$ .................... C07C 2/66; B01J 23/04
[52] U.S. Cl. .................... 585/457; 585/446; 585/452; 585/467; 502/344
[58] Field of Search ............ 585/467, 446, 452, 457; 502/344

[56] References Cited

U.S. PATENT DOCUMENTS

| | | | |
|---|---|---|---|
| 3,321,479 | 5/1967 | Eberhardt et al. | 260/268 |
| 3,356,754 | 12/1967 | Wofford | 260/669 |
| 3,368,121 | 7/1972 | McElroy et al. | 260/668 B |
| 3,458,586 | 7/1969 | Langer, Jr. | 260/668 |
| 3,751,501 | 8/1973 | Kamienski et al. | 260/668 |
| 4,316,820 | 2/1982 | Wieder et al. | 252/431 N |

*Primary Examiner*—Asok Pal
*Assistant Examiner*—P. Achutamurthy
*Attorney, Agent, or Firm*—Carl D. Corvin

[57] ABSTRACT

A process is provided comprising contacting a hydrocarbyl alkali metal compound with a nitrogen-containing compound in the presence of an aromatic compound and at least one alpha-olefin. Optionally, a catalytic support is present during this contacting. In another embodiment of this invention a process is provided comprising: (a) contacting a hydrocarbyl alkali metal compound with a nitrogen-containing compound in the presence of an aromatic compound; and thereafter (b) recovering an aromatic/alkali metal/nitrogen complex; and thereafter (c) contacting said aromatic/alkali metal/nitrogen complex with an alpha-olefin. Optionally, a catalytic support is present during steps a, b, and c.

13 Claims, No Drawings

ALKENE ADDITION PROCESS

BACKGROUND OF THE INVENTION

This invention relates to a process for the addition of an alkene to another compound.

Alkylation, in general, is a process involving the addition of an alkyl group. Specifically, the term is used in the art to apply to various methods, including both thermal and catalytic processes, for bringing about the union of paraffinic hydrocarbons with olefins. Alkylation reactions are important throughout synthetic organic chemistry. For example, the process is especially effective in yielding gasoline of high octane number and low boiling range which are useable as aviation fuels.

Dimerization, in general, is a process involving the addition of an alkene to another alkene which has the same molecular structure. Dimerization processes are important in organic chemistry for a variety of reasons. For example, dimerization reactions are used to form higher alpha-olefins from lower alpha-olefins thereby providing higher molecular weight monomers which can then be polymerized. For example, propylene can be dimerized to form 4-methyl-1-pentene which in turn can be polymerized into poly(4-methyl-1-pentene). Currently, a preferred method in the art to perform dimerization reactions involves using an alkali metal on an alkali metal carbonate. However, these alkali metal/alkali metal carbonate catalyst systems tend to suffer from severe degradation which can lead to reactor plugging and shorter catalyst life. Additionally, it has been theorized that the conversion of an alkali metal to an active species can result in the expansion of the alkali metal in the alkali metal carbonate to the point that the catalytic system starts to break down. Therefore, methods to produce an active species without the use of an elemental alkali metal would be both scientifically and economically valuable.

SUMMARY OF THE INVENTION

It is an object of this invention to provide an improved alkene addition process.

These and other objects of this invention will become apparent to those skilled in the art from the following detailed description of the invention.

In accordance with this invention, a process is provided comprising contacting a hydrocarbyl alkali metal compound with a nitrogen-containing compound in the presence of an aromatic compound and at least one alpha-olefin. Optionally, a catalytic support is present during this contacting.

In another embodiment of this invention a process is provided comprising: (a) contacting a hydrocarbyl alkali metal compound with a nitrogen-containing compound in the presence of an aromatic compound: and thereafter (b) recovering an aromatic/alkali metal/nitrogen complex, and thereafter (c) contacting said aromatic/alkali metal/nitrogen complex with an alpha-olefin. Optionally, a catalytic support is present during steps a, b, and c.

DETAILED DESCRIPTIONS OF THE INVENTION

Hydrocarbyl Alkali Metal Compound

The hydrocarbyl alkali metal compounds useful in forming the aromatic/alkali metal/nitrogen complexes used in this invention can be characterized as follows. The hydrocarbyl group of the hydrocarbyl alkali metal compound can be a linear or branched alkyl or aryl and can contain from 1 to 20 carbon atoms in the molecule. More preferably, the hydrocarbyl group contains from 2 to 16 carbon atoms and most preferably the hydrocarbyl group contains from 3 to 12 carbon atoms in the molecule. However, it is preferred that the hydrocarbyl group be non-reactive in an alkene addition reaction. This means, in general, that the hydrocarbyl group should not contain any oxygen atoms, nor acid groups, which could interfere with the alkene addition reaction. Examples of suitable hydrocarbyl alkali metal compounds useful in this invention, are methyl lithium, ethyl lithium, propyl lithium, butyl lithium, butyl sodium, butyl potassium, butyl rubidium, butyl cesium, benzyl lithium, and phenyl lithium.

Nitrogen Containing Compound

The nitrogen-containing compounds useful in forming the aromatic/alkali metal/nitrogen complexes used in this invention can usually be characterized by one of the general formula shown below.

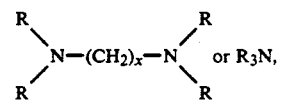

wherein each R group is independently selected from the group consisting of hydrogen and alkyl radicals of 1 to 20 carbon atoms, inclusive and X is an integer between 1 and 10, inclusive. However, it is preferred that the alkyl radicals be non-reactive in an alkene addition reaction. This means, in general, that the alkyl radical should not contain any oxygen atoms, nor any acid groups, which could interfere with the alkene addition reaction. Examples of suitable nitrogen-containing compounds, conforming to the general formulas above are N,N,N',N'-tetramethylenediamine, N,N,N',N'-tetramethylmethylenediamine, N-methylpyrrolidine, triethylamine, and trimethylamine. Other examples of compounds useful in this invention, which do not conform to the above formulas, are N,N,N',N'-tetramethyl-1,3-butanediamine, N,N-dimethyl-1,4-piperazine, triethylenediamine, sparteine, and N,N,N',N'-tetramethyl-1,2-cyclohexanediamine. While the formulas have been provided as a guide to the types of compounds that will work, the essential feature of these compounds is their ability to form a substantially stable resonance group complex with an alkali metal.

Aromatic Compounds

The aromatic compounds useful in forming the aromatic/alkali metal/nitrogen complexes used in this invention can be characterized by following. In one form the aromatic compound can be methyl benzene. Other compounds which could be used are those which have a methyl benzene like structure. Suitable examples of such compounds include, but are not limited to, 1,2 dimethyl-benzene, 1,3 dimethyl-benzene, 1,4-dimethyl-benzene, and 1,3,4-trimethylbenzene. In general, the aromatic compound should not contain any oxygen atoms, nor acid groups, which could interfere with the alkene addition reaction. A general formula for structures which obey the above limitations is

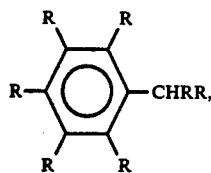

wherein each R is independently selected from the group consisting of hydrogen, alkyl, aryl, and/or alkylaryl. This formula and the above compounds are given as examples only and are not meant to be unduly limiting of the reasonable scope of the vast numbers of compounds which can be used as the aromatic compound.

Alpha-Olefin Compounds

The alpha-olefin compounds useful in this invention can be characterized by the following:

(1) the alpha-olefin should have between 3 and 20 carbon atoms inclusive in the molecule;

(2) the alpha-olefin should not contain any oxygen atoms or acid groups, and (3) the alpha-olefin can be linear or branched.

Examples of suitable alpha-olefins useful in this invention include, but are not limited to, propylene, isobutylene, 1-butene, 3-methyl-1-butene, 1-pentene, 3-methyl-1-pentene, 4-methyl-1-pentene, 1-hexene, 3-ethyl-1-hexene, 1-octene, 1-decene, and mixtures thereof.

Procedures to Make the Aromatic/Alkali Metal/Nitrogen Complexes

In general, the process of forming an aromatic/alkali metal/nitrogen complex is accomplished by contacting a hydrocarbyl alkali metal compound (as disclosed above) with a nitrogen-containing compound (as disclosed above) in the presence of an aromatic compound (as disclosed above). This reaction yields, in general, a hydrocarbon and an aromatic/alkali metal/nitrogen complex. The mole ratio of hydrocarbyl alkali metal to the nitrogen-containing compound should be in the range of about 20:1 to about 1:20. Preferably, the mole ratio is in the range of about 10:1 to about 1:10 and most preferably it is in the range of 5:1 to 1:5.

The reaction conditions to form these types of compounds are as follows. The temperature of the reaction should be between about −50° C. to about 350° C., preferably between 0° C. to 200° C., and most preferably between 20° C. to 150° C. The pressure that the reaction can take place at is from about atmospheric to about 10,000 psig, preferably from atmospheric to about 2,000 psig, and most preferably from atmospheric to 1,000 psig. Additionally, this reaction can take place in a solvent provided the solvent is relatively inert and free of compounds which would tend to interfere with the alkene addition reaction. That is, the solvent should be substantially free of compounds which contain acid groups, water or oxygen.

Reacting the Aromatic/Alkali Metal/Nitrogen Complex

After the aromatic/alkali metal/nitrogen complex is formed it can be used either in situ or it can be separated and stored for later use. The aromatic/alkali metal/nitrogen complex and an alpha-olefin (as disclosed above) can be reacted under the same conditions stated above for forming the aromatic/alkali metal/nitrogen complex. An example of an in situ process would be the reacting of n-butyl lithium and tetramethylethylenediamine in an excess of toluene and a slight amount of propylene. (an excess of toluene is a molar ratio of toluene to lithium of greater than 1:1 but less than 100:1) (a slight amount of propylene is a molar ratio of propylene to lithium of less than 1:1 but more than 1:100). In general, these compounds would react to yield n-butene, an aromatic/lithium/tetramethylethylenediamine complex, and isobutylbenzene, which is the alkene addition product of toluene and propylene. Additionally, some 4-methyl-1-pentene, which is the dimerization product of propylene would be formed. An example of a two-step process would be using the reactants above with only a slight amount of toluene (a slight amount is a molar ratio of toluene to lithium of less than 1:1 but more than 1:100) and no propylene. An aromatic/alkali metal/nitrogen complex would form which could be recovered and stored for later use. This recovered product can be reacted with an alpha-olefin (as described above) to form an alkene addition product. Specifically, if propylene is then added to the aromatic/alkali metal/nitrogen complex, isobutylbenzene would be formed.

Catalytic Support

Regardless of how the above reaction is conducted, a catalytic support can be used in the reaction also. The term "catalytic support" is defined as a composition useful in increasing the entire catalytic system's productivity and value, it is not necessarily meant to be construed as an inert composition which lends nothing to the catalytic system. A catalytic support would allow the catalyst to precipitate on and/or impregnate the catalytic support. This would provide an improved catalytic system and reaction site. Examples of catalytic supports are alkali metal carbonates; silica, alumina, silica-alumina, and alumina-phosphates. These catalytic supports are broadly known in the art and are disclosed, for example, in U.S. Pat. Nos. 4,544,790; 4,609,637; 4,656,154; 4,982,043; 4,988,658; 5,001,204; 5,021,379; and 5,026,796; which are hereby incorporated by reference.

EXAMPLES

These examples are provided to assist a person skilled in the art with understanding this invention. The particular reactants, conditions, and the like are intended to be merely illustrative of this invention and are not meant to be construed as unduly limiting the reasonable scope of this invention.

EXAMPLE I

Screening of Reaction Systems

Several reaction systems were tested for alkene addition activity. Solutions containing the reaction system components as listed below in Table I were tested in 250 mL sealed bottles. These bottles were sealed under anhydrous and oxygen-free conditions. Any solid components were placed in the bottle prior to sealing. All of the reaction system liquid components were introduced via syringe into the sealed bottle. The bottles were then agitated to thoroughly mix the contents. The bottles were then heated in an oil bath to a temperature of about 95° C. Dried, polymerization grade propylene was then introduced to the bottle by bubbling it through the reaction system. Periodically, gas samples were removed from the reaction system and analyzed by an HP 5890 gas chromatograph which was equipped with a flame ionization chamber and a capillary column. This gas chromatograph was programmed to start at 45° C. for 6 minutes with a 15° C. per minute increase to 180° C.

TABLE I

| Run | Reaction System Components | Mole Ratio[1] | Activity[2] |
|---|---|---|---|
| 11 | n-BuLi[3] | NA | No |
| 12A | TMEDA[4] + n-BuLi | 10:1 | Yes |
| 12B | TMEDA + n-BuLi | 1:1 | Yes |
| 12C | TMEDA + n-BuLi | 1:10 | Yes |
| 13A | TMEDA + n-BuLi + Toluene | 1:1:4 | Yes |
| 13B | TMEDA + n-BuLi + Toluene | 1:1:1 | Yes |
| 13C | TMEDA + n-BuLi + Toluene | 10:1:1 | Yes |
| 14 | TMEDA + Benzyl Potassium | 10:1 | Yes |
| 15 | TMEDA + Potassium + Naphthalene | 10:1:1 | Yes |
| 16 | THF[5] + Potassium Naphthalene | 10:1:1 | No |

[1]This is the molar ratio between the reaction system components.
[2]Activity was determined by using a gas chromatograph. A "yes" means that alkene addition products were detected. A "no means that there was not any alkene addition products detected.
[3]n-butyl lithium.
[4]tetramethylethylenediamine.
[5]tetrahydrofuran.

As can be seen from the data in Table I, a reaction system that comprised both a hydrocarbon alkali metal compound and a nitrogen-containing compound showed some activity (see Runs 12A-15). Furthermore, those reaction systems which did not contain the proper components failed to show any activity (see Runs 11 and 16).

EXAMPLE II

Production of Alkene Addition Products

A reaction system comprising tetramethylethylenediamine and n-butyl lithium and toluene was further tested for activity. These components (319.5 mL of toluene, 45 mL of tetramethylethylenediamine, and 15 mL of 2.0 molar n-butyl lithium in cyclohexane) were placed in a nitrogen gas purged, 1 liter, stainless steel, stirred tank reactor. The reactor was then pressurized to 20 psig with nitrogen gas. Dried, polymerization grade propylene (275 mL) was then added to the reactor. The reactor was then heated to a temperature of about 95° C. The reactor pressure was in the range of about 600 to 650 psig. After three hours a sample was removed from the reactor and analyzed by an HP 5890 gas chromatograph which was equipped with a flame ionization chamber and a capillary column. This gas chromatograph was programmed to start at 45° C. for 6 minutes with a 15° C. per minute increase to 180° C.

TABLE II

| Compound | Solution[1] | Product[2] |
|---|---|---|
| Propylene | 3.245 | — |
| Butanes | 0.164 | — |
| 4-methyl-1-pentene | 0.340 | 40.9 |
| 4-methyl-2-pentene | 0.074 | 8.9 |
| Hexane | 3.096 | — |
| Toluene | 86.369 | — |
| Tetramethylenediamine | 6.294 | — |
| Isobutylbenzene | 0.144 | 17.3 |
| Other Cx Products[3] | 0.274 | 32.9 |

[1]This is the weight percent of each compound based on the total weight of the compounds in the solution.
[2]This is the weight percent of the products of the solution based on the total weight of the alkene addition products.
[3]These are other single alkene addition products and impurities in the solution.

As can be seen from the above data, several different types of alkene addition products were formed. It should be noted that isobutylbenzene was about 17 percent of the product as shown in the Table.

EXAMPLE III

Another reaction system was tested in accordance with the procedure and reaction system presented in Example II except that the reactor was pressurized to about 550 psig with ethylene and that no propylene was added to the reactor. After allowing the reaction system to react for one hour the reaction was stopped. It was discovered that a waxy, polymeric composition had formed. The approximate weight of this composition was 554 grams. There were substantially no other products in the reactor. Thus, it seems that ethylene would not form a single alkene addition product, but instead forms a multi-alkene addition product.

That which is claimed is:

1. A process to produce a single alkene addition product said process consisting essentially of contacting:

a hydrocarbyl alkali metal compound selected from the group consisting of methyl lithium, ethyl lithium, propyl lithium, butyl lithium, butyl sodium, butyl potassium, butyl rubidium, butyl cesium, benzyl lithium, phenyl lithium, and mixtures thereof; with a nitrogen containing compound wherein said nitrogen-containing compound is characterized by one of the following formulas:

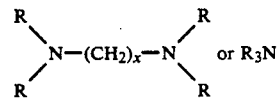

wherein each R group is independently selected from the group consisting of hydrogen and alkyls of 1 to 20 carbon atoms, inclusive, and x is an integer between 1 and 10, inclusive;

in the presence of an aromatic compound wherein said aromatic compound is characterized by the following formula:

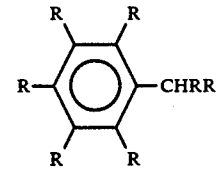

wherein each R is independently selected from the group consisting of hydrogen, alkyl, aryl, and alkylaryl; and also in the presence of at least one alpha-olefin selected from the group consisting of propylene, isobutylene, 1-butene, 3-methyl-1-butene, 1-pentene, 3-methyl-1-pentene, 4-methyl-1-pentene, 1-hexene, 3-ethyl-1-hexene, 1-octene, 1-decene, and mixtures thereof; and recovering said single alkene addition product wherein said single alkene addition product consists essentially of a molecule of said aromatic compound joined to a molecule of said alpha-olefin.

2. A process according to claim 1 wherein said contacting is carried out in the presence of a catalytic support.

3. A process according to claim 2 wherein said catalytic support is selected from the group consisting of alkali metal carbonates, silicas, aluminas, alumina-silicas, alumina-phosphates, and mixtures thereof.

4. A process according to claim 2 wherein said catalytic support comprises potassium carbonate.

5. A process according to claim 1 wherein said hydrocarbyl alkali metal compound is butyl lithium.

6. A process according to claim 1 wherein said nitrogen-containing compound is selected from the group consisting of tetramethylethylenediamine, triethylenediamine, triethylamine, and mixtures thereof.

7. A process according to claim 1 wherein said nitrogen-containing compound is tetramethylethylenediamine.

8. A process according to claim 1 wherein said aromatic compound is selected from the group consisting of toluene, 1,2-dimethyl-benzene, 1,3-dimethyl-benzene, 1,4-dimethyl-benzene, 1,3,4-trimethyl-benzene, and mixtures thereof.

9. A process according to claim 1 wherein said aromatic compound is toluene.

10. A process according to claim 1 wherein said contacting takes place at a temperature between $-50°$ and $350°$ C. and a pressure between atmospheric and 10,000 psig.

11. A process according to claim 1 wherein said aromatic compound is toluene, said alpha-olefin is propylene, and said single alkene addition product is isobutylbenzene.

12. A process to produce isobutylbenzene said process consisting essentially of contacting butyl lithium with tetramethylethylenediamine in the presence of toluene and propylene and recovering said isobutylbenzene.

13. A process to produce isobutylbenzene said process consisting essentially of contacting butyl lithium with tetramethylethylenediamine in the presence of toluene, and thereafter, introducing propylene and recovering said isobutylbenzene.

* * * * *